United States Patent
Tsai et al.

(10) Patent No.: US 10,385,373 B2
(45) Date of Patent: Aug. 20, 2019

(54) HIGH-PURITY GALACTOOLIGOSACCHARIDE COMPOSITIONS, PREPARATIONS, AND APPLICATIONS THEREOF

(71) Applicant: KING-PREBIOTICS BIOTECHNOLOGY (TW) CO., LTD., New Taipei (TW)

(72) Inventors: Chang-Lung Tsai, New Taipei (TW); Ping-Ju Tsai, New Taipei (TW)

(73) Assignee: KING-PREBIOTICS BIOTECHNOLOGY (TW) CO., LTD., New Taipei (TW)

( * ) Notice: Subject to any disclaimer, the term of this patent is extended or adjusted under 35 U.S.C. 154(b) by 0 days.

(21) Appl. No.: 15/902,409

(22) Filed: Feb. 22, 2018

(65) Prior Publication Data

US 2018/0179566 A1 Jun. 28, 2018

Related U.S. Application Data

(62) Division of application No. 15/399,545, filed on Jan. 5, 2017, now Pat. No. 10,190,142.

(60) Provisional application No. 62/286,808, filed on Jan. 25, 2016.

(51) Int. Cl.

| | |
|---|---|
| *C12P 19/04* | (2006.01) |
| *A23L 33/10* | (2016.01) |
| *A23L 2/52* | (2006.01) |
| *A61K 31/702* | (2006.01) |
| *C07H 3/06* | (2006.01) |
| *C12P 19/00* | (2006.01) |
| *C12P 19/14* | (2006.01) |
| *A23L 33/21* | (2016.01) |
| *A61K 9/00* | (2006.01) |

(52) U.S. Cl.
CPC .............. *C12P 19/04* (2013.01); *A23L 2/52* (2013.01); *A23L 33/10* (2016.08); *A23L 33/21* (2016.08); *A61K 9/0019* (2013.01); *A61K 31/702* (2013.01); *C07H 3/06* (2013.01); *C12P 19/00* (2013.01); *C12P 19/14* (2013.01); *A23V 2002/00* (2013.01)

(58) Field of Classification Search
CPC . A23L 2/52; A23L 33/10; A23L 33/21; A23V 2002/00; A61K 31/702; A61K 9/0019; C07H 3/06; C12P 19/00; C12P 19/04; C12P 19/14
See application file for complete search history.

(56) References Cited

U.S. PATENT DOCUMENTS

| | | | |
|---|---|---|---|
| 7,883,874 B2 | 2/2011 | Gibson et al. | |
| 9,200,303 B2 | 12/2015 | Giacomelli et al. | |
| 2011/0189342 A1 | 8/2011 | Jeong | |
| 2011/0287072 A1* | 11/2011 | Ritter | A61K 31/702 424/400 |

FOREIGN PATENT DOCUMENTS

| | | |
|---|---|---|
| CN | 102471792 | 12/2014 |
| EP | 1644482 | 10/2014 |
| WO | 2009113030 | 9/2009 |
| WO | 2011093907 | 8/2011 |
| WO | 2015175412 | 11/2015 |

* cited by examiner

*Primary Examiner* — Deborah K Ware
(74) *Attorney, Agent, or Firm* — WPAT, PC

(57) ABSTRACT

Provided is a method of preparing a high-purity galactooligosaccharide composition by fermentation of a low-purity galactooligosaccharide mixture with a yeast strain, *Kluyveromyces lactis* ATCC 8585. The high-purity galactooligosaccharide composition includes at least 99% of galactooligosaccharides selected from the group consisting of galactotriose, galactotetrose, galactooligosaccharides with five or more sugar units, and combinations thereof and lower than 1% of monosaccharides and disaccharides. Also provided is a high-purity galactooligosaccharide composition and applications thereof in regulating blood glucose level and improving gut microbiota. For example, the high-purity galactooligosaccharide composition may be used to manufacture food products, beverages, health food products, nutritional supplements, and pharmaceutical compositions for patients or pets afflicted with diabetes mellitus or lactose intolerance.

7 Claims, 2 Drawing Sheets

HIGH-PURITY GALACTOOLIGOSACCHARIDE COMPOSITIONS, PREPARATIONS, AND APPLICATIONS THEREOF

CROSS-REFERENCE TO RELATED APPLICATION

This application is a Divisional of co-pending U.S. application Ser. No. 15/399,545, filed on Jan. 5, 2017, which claims priority of U.S. Provisional Application No. 62/286,808, filed on Jan. 25, 2016; the entire contents of all of the above-identified applications are incorporated herein by reference.

BACKGROUND OF THE INVENTION

1. Field of the Invention

The present invention relates to a galactooligosaccharide composition, preparation, and application thereof. Particularly, the present invention relates to a high-purity galactooligosaccharide composition and preparation thereof, and a method of regulating blood glucose level and improving gut microbiota with the high-purity galactooligosaccharide composition.

2. The Prior Art

Galactooligosaccharides (GOS) are one type of non-digestible oligosaccharides (NDOs). They are oligosaccharides composed of two to ten galactose units and one terminal glucose moiety, and they are classified into galactobiose, galactotriose, galactotetraose, and galactooligosaccharide with five or more sugar units according to the number of monosaccharide units they contain. Commercial GOS products are mixtures of GOS with different molecular weight that have varied compositions. Due to differences in manufacture process, they contain various amounts of lactose, sucrose, glucose, and galactose. GOS products have a fairly wide application in industry, including food additives and pharmaceutical compositions, and their application fields vary depending on the sugar content of the products. For example, under an ideal condition, GOS products suitable for lactose intolerance patients should contain no lactose, and GOS products for reduced calories should lower monosaccharide content.

The well-known methods of GOS preparation are generally divided into enzymatic transformation and fermentation by microorganisms. However, the crude GOS products obtained by these methods contain residual monosaccharides such as glucose and disaccharides such as lactose. To meet the market requirement, studies in related fields have started to focus on improvement of GOS preparation processes to lower the content of monosaccharides and disaccharides. The proposed strategies include utilization of chromatography or membrane filtration methods such as ultrafiltration and nanofiltration for direct removal of monosaccharides and disaccharides from the crude GOS products, or enzymatic oxidation of monosaccharides and disaccharides to form sugar acids which are subsequently removed by ion exchange chromatography, or depletion of monosaccharides and disaccharides by microbial fermentation. Nevertheless, it is inefficient to remove lactose by chromatography or membrane filtration methods; the enzymatic oxidation process is too costly and difficult to scale-up for industrial production; and microbial fermentation requires two or more strains of bacteria or fungi to effectively remove monosaccharides and disaccharides, which complicates the manufacture process.

Accordingly, there is a need to develop a method for industrial production of a high-purity GOS composition with low cost and simplified process in order to provide a GOS composition free of monosaccharides and disaccharides.

SUMMARY OF THE INVENTION

As a result, one aspect of the present invention is to provide a method of preparing a high-purity galactooligosaccharide composition, comprising the steps of: (1) providing a reaction solution comprising a low-purity galactooligosaccharide mixture; and (2) adding a *Kluyveromyces lactis* strain to the reaction solution to carry out a fermentation process to obtain the high-purity galactooligosaccharide composition, wherein the *Kluyveromyces lactis* strain is *Kluyveromyces lactis* ATCC 8585, and wherein the high-purity galactooligosaccharide composition comprises at least 99% w/w of galactooligosaccharides selected from the group consisting of galactotriose, galactotetraose, galactooligosaccharide with five or more sugar units, and combinations thereof and lower than 1% w/w of monosaccharides and disaccharides.

In one embodiment of the present invention, the low-purity galactooligosaccharide mixture has a purity of 55-60%; the reaction solution is 30-35 degree Brix; the *Kluyveromyces lactis* strain is added at an amount of at least about 0.8% of the low-purity galactooligosaccharide mixture by dry mass; the fermentation process is carried out at 30-40° C. for 24-72 hours; and the high-purity galactooligosaccharide composition is 100% galactooligosaccharides selected from the group consisting of galactotriose, galactotetraose, galactooligosaccharide with five or more sugar units, and combinations thereof.

In another aspect, the present invention provides a high-purity galactooligosaccharide composition, comprising at least 99% w/w of galactooligosaccharides selected from the group consisting of galactotriose, galactotetraose, galactooligosaccharide with five or more sugar units, and combinations thereof and lower than 1% w/w of monosaccharides and disaccharides.

In one embodiment of the present invention, the high-purity galactooligosaccharide composition is obtained from a fermentation process by a *Kluyveromyces lactis* strain, wherein the *Kluyveromyces lactis* strain is *Kluyveromyces lactis* ATCC 8585. The high-purity galactooligosaccharide composition comprises 48-57% w/w galactotriose, 25-32% w/w galactotetraose, and 15-22% w/w galactooligosaccharide with five or more sugar units.

In yet another aspect, the present invention provides a method of regulating blood glucose level in a subject, comprising administering to the subject an effective amount of a high-purity galactooligosaccharide composition, wherein the high-purity galactooligosaccharide composition comprises at least 99% w/w of galactooligosaccharides selected from the group consisting of galactotriose, galactotetraose, galactooligosaccharide with five or more sugar units, and combinations thereof and lower than 1% w/w of monosaccharides and disaccharides.

In still another aspect, the present invention provides a method of improving gut microbiota in a subject, comprising administering to the subject an effective amount of a high-purity galactooligosaccharide composition, wherein the high-purity galactooligosaccharide composition comprises at least 99% w/w of galactooligosaccharides selected from the group consisting of galactotriose, galactotetraose, galactooligosaccharide with five or more sugar units, and combinations thereof and lower than 1% w/w of monosaccharides and disaccharides.

In one embodiment of the present invention, the high-purity galactooligosaccharide composition comprises 48-57% w/w galactotriose, 25-32% w/w galactotetraose, and 15-22% w/w galactooligosaccharide with five or more sugar units, and it is administered daily at a dose of at least 0.16 g/kg body weight for a human subject, which is comparable to daily uptake of at least 9.7 g for a 60 kg adult; the subject is afflicted with diabetes mellitus; and the high-purity galactooligosaccharide composition is a food product, a beverage, a health food product, a nutritional supplement, or a pharmaceutical composition.

The method of preparing a high-purity galactooligosaccharide (GOS) composition of the present invention utilizes a single yeast strain, Kluyveromyces lactis ATCC 8585, to carry out a fermentation process to directly obtain a high-purity GOS composition with a purity of 99% or more, or even to obtain a high-purity GOS composition with a purity of 100%. Therefore, the method of the present invention prepares a GOS composition free of monosaccharides and disaccharides by a more simplified high-purity GOS manufacture process compared with the conventional techniques, and this method is applicable to large-scale production. The high-purity GOS composition of the present invention can effectively reduce blood glucose level in diabetes mellitus patients, and also improve gut microbiota to sustain gut health. Thus, it can be used to develop methods of regulating blood glucose level and improving gut microbiota and to prepare compositions for these purposes. For example, the high-purity GOS composition of the present invention may be used to manufacture food products, beverages, health food products, nutritional supplements, and pharmaceutical compositions for patients or pets afflicted with diabetes mellitus or lactose intolerance.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Definition

Figure 1:
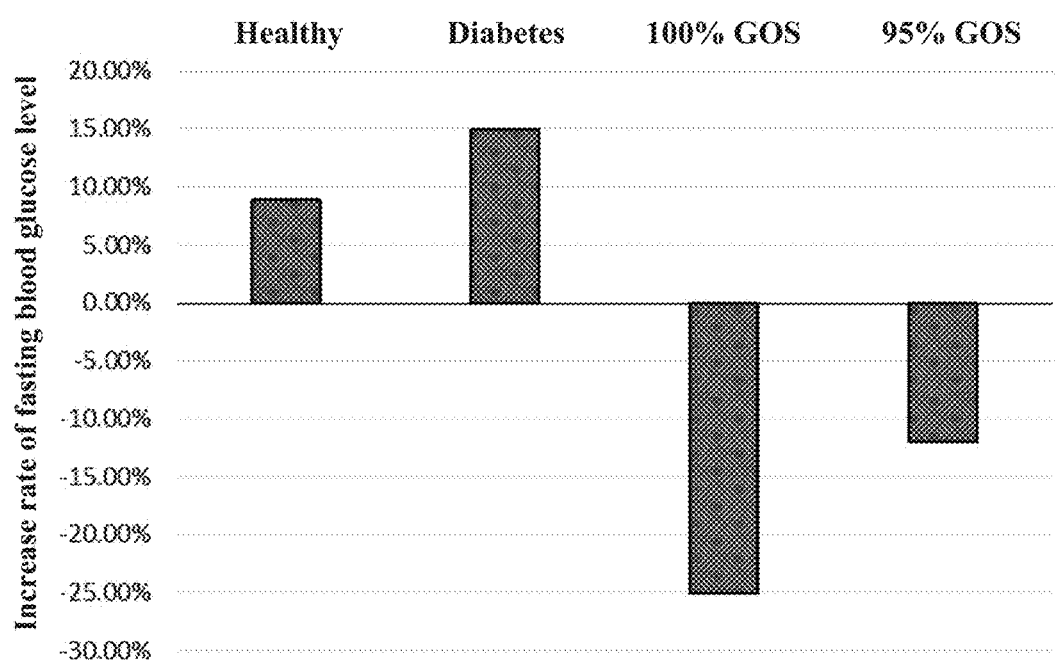
FIG. 1 shows the ability of the high-purity GOS composition of the present invention with a purity of 100% to reduce the increase rate of fasting blood glucose level in diabetes mellitus rats.

Numerical quantities given herein are approximate, and experimental values may vary within 20 percent, preferably within 10 percent, and most preferably within 5 percent. Thus, the term "about" used herein refers to within 20 percent, preferably within 10 percent, and most preferably within 5 percent of a given value or range.

As used herein, the term "effective amount" refers to the dosage of the high-purity galactooligosaccharide composition that can reduce fasting blood glucose level or improve gut microbiota in animals and humans. The appropriate effective dosage may vary depending on the organism or individual treated but can be determined experimentally using various techniques, including a dose escalation study.

As used herein, the term "purity" refers to an area ratio of the sum of the signals of galactotriose, galactotetraose, and galactooligosaccharide with five or more sugar units to the overall signal of sugar in chromatograms of high performance liquid chromatography (HPLC).

The present invention provides a high-purity galactooligosaccharide (GOS) composition and a method of preparing the same. For the preparation, a low-purity GOS mixture with a purity of about 55-60%, which is used as the raw material, is diluted with distilled water to form a reaction solution that is 30-35 degree Brix. Next, 1% yeast extract and 0.3-0.8% Kluyveromyces lactis ATCC 8585 are added into the reaction solution for a fermentation process to be carried out at 30-40° C. for 24-72 hours. In one embodiment of the present invention, the fermentation process is carried out in a 30-ton fermentor with a 20-ton fermentation solution at pH 5.0-5.6 and at the ventilation rate of 3-5 L/min and the agitation speed of 150 rpm. When the content of monosaccharides and disaccharides in the fermentation solution is lower than 1% w/w and the purity of the GOS product reaches at least 99%, the fermentation solution is heated to 90-95° C. to stop the fermentation process, and an initial product of the high-purity GOS composition of the present invention is obtained.

To obtain an edible high-purity GOS composition without impurities, the fermentation solution is subsequently centrifuged to precipitate the yeast and the yeast extract therein and then filtered by a Perlite filter to remove the precipitates. In one embodiment of the present invention, the centrifugation step was performed at 6-10° C. for 5-10 hours at 15000 rpm. Next, the fermentation solution is filtered through activated charcoal to remove pigments, subjected to cation exchange resin and anion exchange resin treatment to remove minerals, and subjected to evaporation concentration for dehydration, so that the final product of the high-purity GOS composition of the present invention is obtained. The sugar content of the high-purity GOS composition is lower than 1% w/w of monosaccharides and disaccharides, about 48-57% w/w galactotriose, about 25-32% w/w galactotetraose, and about 15-22% w/w GOS with five or more sugar units.

Methods and Materials

Materials

The Kluyveromyces lactis ATCC 8585 was purchased from American Type Culture Collection (Manassas, USA). Yeast extract may be purchased from, but not limited to, Angel Yeast Company (China). Cation exchange resin based on sulfonated styrene-clivinylbenzene copolymer and anion exchange resin based on styrene-clivinylbenzene copolymer with tertiary amine groups were purchased from Sigma-Alderich (USA).

Preparation of Low-Purity GOS Mixture, the Raw Material

The raw material used for preparation of the high-purity GOS composition in the present invention, that is, the low-purity GOS mixture, may be purchased directly from New Francisco (Yunfu City) Biotechnology Corporation Limited (China) or it may be prepared from transformation of lactose by β-galactosidase of *Bacillus circulans*. The low-purity GOS mixture has a purity of about 55-60%, preferably 57%. Transformation of lactose was carried out at 30-50° C. for 48-72 hours with a starting concentration of 40-60% w/w of lactose.

Composition Analysis of the Fermentation Solution

Sugar content of the fermentation solution was analyzed using HPLC equipped with a calcium-type cation exchange column (CARBOSep CHO-620, Transgennomic, USA). Samples of the fermentation solution were diluted to a concentration of 2% with water, and signals of sugars in the eluent were detected by a refractive index detector. The retention time of peak and the signal intensity for each type of sugars separated were recorded. A quantitative analysis was performed by comparing to signals of the sugar standards. The peak area of each sugar signal in the chromatograms was used to calculate the proportion of each sugar in the total sugar.

Gut Microbiota Test

About 1 g of rat appendix contents was added to a test tube containing 9 mL of a sterile anaerobic dilution buffer (0.5 g cysteine, 4.5 g potassium dihydrogen phosphate, 6 g sodium hydrogen phosphate, 1 g Tween20, 2 g gelatin, dissolved in 1 L deionized water) and 5 glass beads, and these contents were mixed to form a homogeneous solution by a test tube shaker. Ten-fold serial dilutions of the homogeneous solution were performed with the anaerobic dilution buffer under anaerobic condition. 0.1 mL of the appropriately diluted homogeneous solution was plated onto a *Bifidobacteria* iodoacetatte medium-25 (BIM-25; 51 g reinforced clostridial agar, 0.02 g nalidixic acid, 0.0085 g polymyxin B sulfate, 0.05 g kanamycin sulfate, 0.0025 g iodoacetic acid, 0.025 g triphenyltetrazolium chloride, dissolved in 1 L deionized water) or a *Lactobacillus* selective MRS medium (55 g Lactobacilli MRS broth (Difco), 20 g agar, 1.2 mL acetic acid, 3 g phenethyl alcohol, 0.04 g bromcresol green, dissolved in 1 L deionized water), and the plates were placed in an anaerobic incubator for 16 hours at 37° C. for counting colony forming units (cfu) of *Bifidobacteria* or *Lactobacillus*. For counting colony forming units of *Clostridium*, 0.1 mL of the appropriately diluted homogeneous solution mentioned above was plated onto a TSC medium (15 g tryptose, 5 g yeast extract, 5 g soytone, 1 g ferric ammonium citrate, 1 g sodium metabisulfite, 20 g agar, dissolved in 1 L deionized water) supplemented with egg yolk emulsion. This medium, after dried, was poured onto a 5-10 mL TSC medium without egg yolk emulsion, and then placed in an anaerobic incubator for 16 hours at 37° C. The number of bacteria in the gut was calculated according to the following equation:

$$\frac{\text{Colony forming units } (cfu)}{\text{Volume of the homogeneous solution plated (mL)}} \times \frac{1000 \text{ } (\mu L)}{1 \text{ }(mL)} \times$$

$$\frac{1}{\text{Concentration of the homogeneous solution (mL)}} \times \text{Fold of dilution} = \frac{\text{Colony forming units } (cfu)}{\text{Appendix content (g)}}$$

Example 1

Evaluation of the Effect of Sugar Content of the Reaction Solution on the Purity of the GOS Product To evaluate the effect of sugar content of the reaction solution on the purity of the GOS product, a low-purity GOS mixture with a purity of 57% was diluted with distilled water to form three reaction solutions that were 30, 35, and 40 degree Brix and named Group A, B, and C, respectively. The reaction solutions were adjusted to pH 5.0-5.6. Next, 1% by weight of yeast extract (on a dry basis of the low-purity GOS mixture) was added to the reaction solutions and heated for dissolution. When the reaction solutions were cooled to 30-40° C., 0.5% by weight of *Kluyveromyces lactis* ATCC 8585 was added (on a dry basis of the low-purity GOS mixture). After fermentation with agitation and ventilation for 24 and 48 hours, the fermentation solutions were sampled for composition analysis by HPLC.

The fermentation results of the reaction solutions with different sugar contents were shown in TABLE 1. According to the composition analysis, after fermentation of 24 hours, the proportions of GOS with three or more sugar units in the total sugar of the fermentation solutions were 79.3% w/w, 82.6% w/w, and 67.9% w/w for Groups A, B, and C, respectively. After fermentation of 48 hours, the proportions of GOS with three or more sugar units in the total sugar of the fermentation solutions increased to 92.3% w/w, 95.4% w/w, and 80.5% w/w for Groups A, B, and C, respectively. The results indicate that *Kluyveromyces lactis* ATCC 8585 possesses the best ability to deplete monosaccharides and disaccharides when the reaction solution is 35 degree Brix.

TABLE 1

Effect of sugar content of the reaction solution on the purity of the GOS product

| Groups | Added amount of yeast | Degree Brix | Proportion of GOS with three or more sugar units | |
|--------|----------------------|-------------|----------|----------|
|        |                      |             | 24 hours | 48 hours |
| A | 0.5% | 30 | 79.3% | 92.3% |
| B | 0.5% | 35 | 82.6% | 95.4% |
| C | 0.5% | 40 | 67.9% | 80.5% |

Example 2

Evaluation of the Effect of the Added Amount of Yeast on the Purity of the GOS Product To evaluate the effect of the added amount of yeast on the purity of the GOS product, a low-purity GOS mixture with a purity of 57% was diluted with distilled water to form a reaction solution that was 35 degree Brix, and the reaction solution was adjusted to pH 5.0-5.6. Next, 1% by weight of yeast extract (on a dry basis of the low-purity GOS mixture) was added to the reaction solution and heated for dissolution. When the reaction solution was cooled to 30-40° C., 0.3%, 0.5%, or 0.8% by weight of *Kluyveromyces lactis* ATCC 8585 was added (on a dry basis of the low-purity GOS mixture) to form three reaction solutions named Group D, E, and F, respectively. After fermentation with agitation and ventilation for 24 and 48 hours, the fermentation solutions were sampled for composition analysis by HPLC.

The fermentation results of the reaction solutions with different added amounts of yeast were shown in TABLE 2. According to the composition analysis, after fermentation of 24 hours, the proportions of GOS with three or more sugar units in the total sugar of the fermentation solutions were 76.4% w/w, 82.0% w/w, and 90.2% w/w for Groups D, E, and F, respectively. After fermentation of 48 hours, the proportions of GOS with three or more sugar units in the total sugar of the fermentation solutions increased to 87.8% w/w, 95.7% w/w, and 100% w/w for Groups D, E, and F, respectively. The results indicate that the GOS product containing GOS with three or more sugar units reaches a purity of above 95% when the added amount of *Kluyveromyces lactis* ATCC 8585 is 0.5%, and the GOS product containing GOS with three or more sugar units reaches a purity of 100% when the added amount of the yeast is 0.8%.

TABLE 2

Effect of the added amount of yeast on the purity of the GOS product

| Groups | Added amount of yeast | Degree Brix | Proportion of GOS with three or more sugar units 24 hours | 48 hours |
|---|---|---|---|---|
| D | 0.3% | 35 | 76.4% | 87.8% |
| E | 0.5% | 35 | 82.0% | 95.7% |
| F | 0.8% | 35 | 90.2% | 100.0% |

According to Examples 1-2 previously described, addition of the single yeast strain, *Kluyveromyces lactis* ATCC 8585, to a low-purity GOS mixture for a fermentation process may completely deplete monosaccharides and disaccharides in a fermentation solution, and thus an initial product of the high-purity GOS composition of the present invention free of monosaccharides and disaccharides may be obtained.

Example 3

Composition Analysis of the High-Purity GOS Composition from Different Batches

For a more detailed analysis, inedible impurities and water were first removed from the initial product of the high-purity GOS composition previously described, and then HPLC was used to analyze the sugar content of the high-purity GOS composition of the present invention. A low-purity GOS mixture with a purity of 57% was first diluted with distilled water to form a reaction solution that was 35 degree Brix, and the reaction solution was adjusted to pH 5.0-5.6. Next, 1% by weight of yeast extract (on a dry basis of the low-purity GOS mixture) was added to the reaction solution and heated for dissolution. When the reaction solution was cooled to 30-40° C., 0.8% by weight of *Kluyveromyces lactis* ATCC 8585 was added (on a dry basis of the low-purity GOS mixture). After fermentation with agitation and ventilation for 48-72 hours, the fermentation solution is heated to 90-95° C. to stop the fermentation process once the proportion of GOS with three or more sugar units in the fermentation solution reaches 100%. This fermentation solution containing the high-purity GOS product was centrifuged to precipitate the yeast and the yeast extract therein and filtered by a Perlite filter to remove the precipitates. It was further decolorized by activated charcoal which removes pigments produced during the fermentation process, subjected to cation exchange resin and anion exchange resin treatment to remove minerals, and finally subjected to evaporation concentration, and then high-purity GOS syrup was obtained. A high-purity GOS powder was produced therefrom after a drying step.

TABLE 3 shows sugar content of the high-purity GOS powder form three batches. In general, the high-purity GOS composition of the present invention contains lower than 1% w/w of monosaccharides and disaccharides, preferably no monosaccharides and disaccharides at all, about 48-57% w/w galactotriose, about 25-32% w/w galactotetraose, and about 15-22% w/w GOS with five or more sugar units.

TABLE 3

Sugar content of the high-purity GOS powder from different batches

| Batch | Monosaccharides | Disaccharides (lactose included) | Galactotriose | Galactotetraose | GOS with five or more sugar units |
|---|---|---|---|---|---|
| 1 | 0% | 0% | 56.5% | 27.1% | 16.4% |
| 2 | 0% | 0% | 53.6% | 28.2% | 18.0% |
| 3 | 0% | 0% | 48.9% | 31.8% | 19.3% |

Example 4

Blood Glucose Lowering Effect of the High-Purity GOS Composition

Sprague Dawley (abbreviated as SD) rats induced to have diabetes mellitus were employed as a model in this example to compare the blood glucose lowering effect of the high-purity GOS composition of the present invention with a purity of 100% and a GOS composition with a purity of 95%. First, 40 SD rats acclimatized for 2 weeks were randomly assigned into the following four groups each having 10 rats: the healthy group, the diabetes group, the 100% GOS group, and the 95% GOS group. All the groups were fed with standard diet (AIN-93) during acclimatization. All the groups except the healthy group were intraperitoneally injected with 65 mg/kg streptozotocin (STZ) and 230 mg/kg nicotinamide for induction of diabetes, which led to a fasting blood glucose level of above 230±10 mg/dL (the criteria for diabetes) for the three groups of rats. Next, the healthy group and the diabetes group were fed with standard diet continuously, while the 95% GOS group and the 100% GOS group were tube fed with saline containing the dissolved GOS composition with a purity of 95% and the dissolved high-purity GOS composition of the present invention with a purity of 100%, respectively. The dose for administration of each of the two GOS compositions was 1 g/kg body weight/day. TABLE 4 shows sugar content of the GOS composition with a purity of 95% and the high-purity GOS composition of the present invention with a purity of 100% used in this example. Fasting blood glucose level, the blood glucose level after fasting for 24 hours, of the rats was measured using a commercial kit (Quick Auto Neo GLU-HK) based on hexokinase assay and a HITACHI 7080 biochemistry analyzer (Japan) prior to and after two weeks of feeding, and the change in the fasting blood glucose level was determined.

TABLE 4

Sugar content of different GOS compositions

| Purity of GOS | Sugar content | | | | |
|---|---|---|---|---|---|
| | Monosaccharides | Disaccharides | Galactotriose | Galactotetraose | GOS with five or more sugar units |
| 95% | 0.8% | 3.9% | 45.3% | 30.0% | 20.1% |
| 100% | 0% | 0% | 56.5% | 27.1% | 16.4% |

The fasting blood glucose level of the rats and the increase rate of the fasting blood glucose level were shown in TABLE 5 and FIG. 1. Compared with the healthy group, the diabetes group exhibited significantly increased fasting blood glucose level. However, the 95% GOS group and the 100% GOS group showed significantly reduced fasting blood glucose levels after feeding of GOS, and the 100% GOS group showed the greatest reduction in fasting blood glucose level, a 25% reduction. The results indicate that the high-purity GOS composition of the present invention possesses the prominent blood glucose lowering effect due to a decreased content of monosaccharides and disaccharides and the increased proportions of galactotriose. The dose of the high-purity GOS composition of the present invention administered to rats in this example was 1 g/kg body weight/day, which was converted to a daily dose of about 0.16 g/kg body weight for a human subject based on the guideline on estimating the maximum safe starting dose in initial clinical trials for therapeutics in adult healthy volunteers issued by U.S. Food and Drug Administration (FDA) in 2005.

TABLE 5

Blood glucose lowering effect of different GOS compositions

| Group | Fasting blood glucose level (mg/dL) | | Increase rate of fasting blood glucose level (%) |
|---|---|---|---|
| | Week 0 | Week 2 | |
| Healthy | 136.3 | 148.5 | 9.0% |
| Diabetes | 338.8 | 389.6 | 15.0% |
| 100% GOS | 391.3 | 293.5 | −25.0% |
| 95% GOS | 389.7 | 342.8 | −12.0% |

Example 5

Improving Effect of the High-Purity GOS Composition on Gut Microbiota

SD rats induced to have diabetes mellitus were employed as a model in this example to compare the effect of the high-purity GOS composition of the present invention with a purity of 100% and a GOS composition with a purity of 95% on improving gut microbiota of a subject. Similar to the operation described in Example 4, 40 SD rats were randomly assigned into the following four groups each having 10 rats: the healthy group, the diabetes group, the 100% GOS group, and the 95% GOS group. After the treatment for induction of diabetes, the healthy group and the diabetes group were fed with standard diet, while the 95% GOS group and the 100% GOS group were tube fed with saline containing the dissolved GOS composition with a purity of 95% and the dissolved high-purity GOS composition of the present invention with a purity of 100%, respectively. The dose for administration of each of the two GOS compositions was 1 g/kg body weight/day. TABLE 4 shows sugar content of the GOS composition with a purity of 95% and the high-purity GOS composition of the present invention with a purity of 100% used in this example. The rat gut microbiota was analyzed prior to and after two weeks of feeding.

Figure 2:
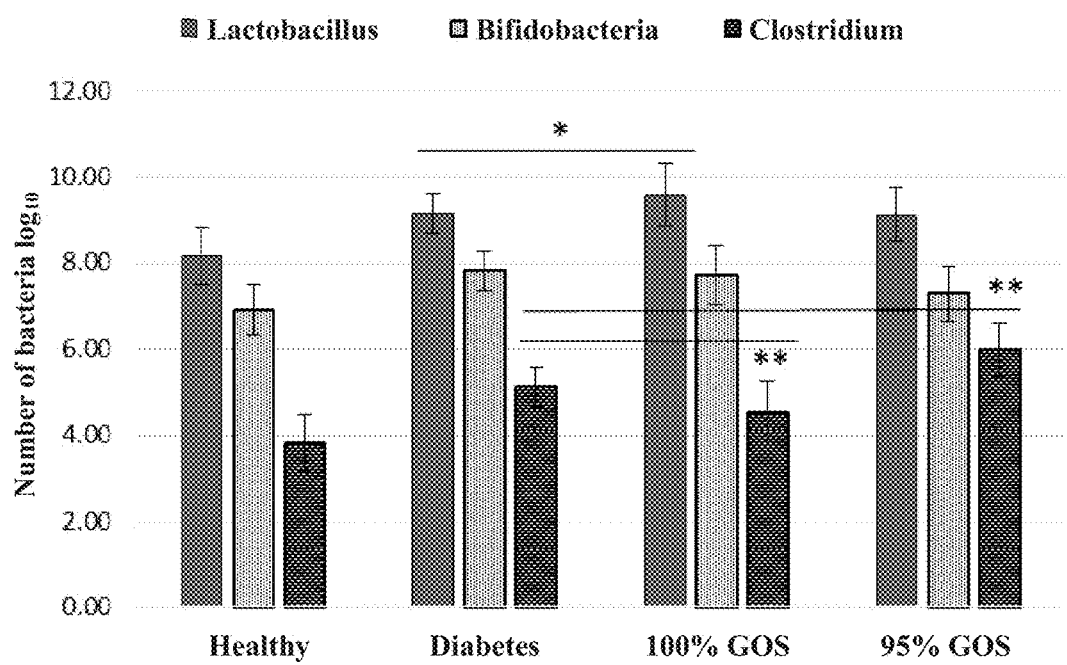
FIG. 2 shows the ability of the high-purity GOS composition of the present invention with a purity of 100% to promote growth of probiotic bacteria and to inhibit growth of harmful bacteria; * indicates $p<0.1$, ** indicates $p<0.05$.

FIG. 2 shows the estimated number of the probiotic bacteria such as *Lactobacillus* and *Bifidobacteria* and that of the harmful bacteria such as *Clostridium*, in the gut of the rats. Compared with the diabetes group, the number of *Bifidobacteria* significantly increased and the number of *Clostridium* decreased in the gut of the 100% GOS group. Comparatively, no increase in the number of *Bifidobacteria* but more growth of *Clostridium* was observed in the 95% GOS group. The results indicate that the high-purity GOS composition of the present invention effectively promotes growth of probiotic bacteria and thus inhibits growth of harmful bacteria, leading to the effective improvement of gut microbiota. The dose of the high-purity GOS composition of the present invention administered to rats in this example was 1 g/kg body weight/day, which was converted to a daily dose of about 0.16 g/kg body weight for a human subject based on the guideline on estimating the maximum safe starting dose in initial clinical trials for therapeutics in adult healthy volunteers issued by U.S. Food and Drug Administration (FDA) in 2005.

In conclusion, the method of preparing a high-purity GOS composition of the present invention utilizes a single yeast strain, *Kluyveromyces lactis* ATCC 8585, to carry out a fermentation process to directly obtain a high-purity GOS composition with a purity of 99% or more. This composition includes at least 99% w/w of GOS selected from the group consisting of galactotriose, galactotetraose, GOS with five or more sugar units, and combinations thereof and lower than 1% w/w of monosaccharides and disaccharides. Preferably, it is 100% GOS selected from the group consisting of galactotriose, galactotetraose, GOS with five or more sugar units, and combinations thereof. The high-purity GOS composition of the present invention can reduce blood glucose level in diabetes mellitus patients more effectively than a GOS composition with a purity of 95% and also prominently improve gut microbiota to sustain gut health. Thus, it can be used to develop methods of regulating blood glucose level and improving gut microbiota and to prepare compositions for these purposes. For example, the high-purity GOS composition of the present invention may be used to manufacture food products, beverages, health food products, nutritional supplements, and pharmaceutical compositions for patients or pets afflicted with diabetes mellitus or lactose intolerance. These products may be powder or liquid or may be ready-to-use. These products may further include a group selected from the group consisting of a food ingredient and a healthy food ingredient. The food ingredient may be, but not limited to, vegetables or meats, and the healthy food ingredient may be, but not limited to, taurine, vitamins, niacin, or other ingredients beneficial for health.

What is claimed is:

1. A method of preparing a high-purity galactooligosaccharide composition, comprising the steps of:
   (1) providing a reaction solution comprising a galactooligosaccharide mixture; and
   (2) adding a *Kluyveromyces lactis* strain to the reaction solution to carry out a fermentation process to obtain a high-purity galactooligosaccharide composition;
   wherein the *Kluyveromyces lactis* strain is *Kluyveromyces lactis* ATCC 8585, and wherein the high-purity galactooligosaccharide composition comprises at least 99% w/w of galactooligosaccharides selected from the group consisting of galactotriose, galactotetraose, galactooligosaccharide with five or more sugar units, and combinations thereof and lower than 1% w/w of monosaccharides and disaccharides.

2. The method of claim 1, wherein the galactooligosaccharide mixture has a purity of 55-60%.

3. The method of claim 1, wherein the reaction solution is 30-35 degree Brix.

4. The method of claim 1, wherein the *Kluyveromyces lactis* strain is added at an amount of at least about 0.8% of the galactooligosaccharide mixture by dry mass.

5. The method of claim 1, wherein the fermentation process is carried out at 30-40° C. for 24-72 hours.

6. The method of claim 1, wherein the high-purity galactooligosaccharide composition is 100% galactooligosaccharides selected from the group consisting of galactotriose, galactotetraose, galactooligosaccharide with five or more sugar units, and combinations thereof.

7. The method of claim 1, wherein the high-purity galactooligosaccharide composition comprises 48-57% w/w galactotriose, 25-32% w/w galactotetraose, 15-22% w/w galactooligosaccharide with five or more sugar units, and lower than 1% w/w of monosaccharides and disaccharides.

* * * * *